United States Patent
Eggenweiler

(10) Patent No.: US 6,960,661 B2
(45) Date of Patent: Nov. 1, 2005

(54) [7-(3-CHLORO-4-METHOXYBENZLAMINO)-1-METHYL-3-PROPYL-1H-PYRAZOLO[4,3-D]PYRIMIDIN-5-YLMETHOXY]ACETIC ACID, SYNTHESIS THEREOF AND INTERMEDIATES USED THEREIN

(75) Inventor: Hans-Michael Eggenweiler, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/470,337

(22) PCT Filed: Dec. 29, 2001

(86) PCT No.: PCT/EP01/15372
§ 371 (c)(1),
(2), (4) Date: Jul. 28, 2003

(87) PCT Pub. No.: WO02/059126
PCT Pub. Date: Aug. 1, 2002

(65) Prior Publication Data
US 2004/0053945 A1 Mar. 18, 2004

(30) Foreign Application Priority Data
Mar. 27, 2001 (DE) .......................... 101 03 647

(51) Int. Cl.[7] .................. C07D 487/04; C07D 231/40
(52) U.S. Cl. ..................... 544/262; 548/371.7
(58) Field of Search ................. 544/262; 548/371.7

(56) References Cited

U.S. PATENT DOCUMENTS

| | | |
|---|---|---|
| 4,666,908 A | 5/1987 | Hamilton |
| 6,130,223 A | 10/2000 | Christadler et al. |

FOREIGN PATENT DOCUMENTS

| | | |
|---|---|---|
| DE | 197 52 952 A | 6/1999 |
| WO | WO 01 18004 A | 3/2001 |

OTHER PUBLICATIONS

West, Anthony R., Solid State Chemistry and its Applications, Wiley, New York, 1988, pp. 358 & 365.*

Dumaitre B et al: "Synthesis and Cyclic GMP Phosphodiesterase Inhibitory Activity of a Series of 6–Phenylpyrazolou3, 4–Dpyrimidones" Journal of Medicinal Chemistry, American Chemical Society. Washington, US, vol. 39, No. 8, 1996, pp. 1635–1644, XP000651134 ISSN: 0022–2623 p. 1635, right–hand column; figure 1.

* cited by examiner

Primary Examiner—Thomas C. McKenzie
(74) Attorney, Agent, or Firm—Millen, White, Zelano & Branigan, P.C.

(57) ABSTRACT

[7-(3-chloro-4-methoxybenzylamino)-1-methyl-3-propyl-1H-pyrazolo[4,3-d]pyrimidin-5-ylmethoxy]acetic acid,

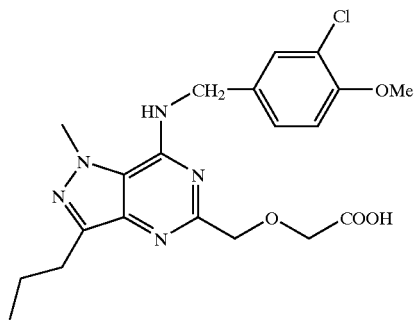

is disclosed, as well as a process for its preperation and intermediates in the process of preparing the same.

4 Claims, No Drawings

[7-(3-CHLORO-4-METHOXYBENZLAMINO)-1-METHYL-3-PROPYL-1H-PYRAZOLO[4,3-D] PYRIMIDIN-5-YLMETHOXY]ACETIC ACID, SYNTHESIS THEREOF AND INTERMEDIATES USED THEREIN

The invention relates to a process for the preparation of [7-(3-chloro-4-methoxybenzylamino)-1-methyl-3-propyl-1H-pyrazolo[4,3-d]pyrimidin-5-ylmethoxy]acetic acid.

This substance specifically inhibits cGMP phosphodiesterase (PDE V).

Compounds of the formula I

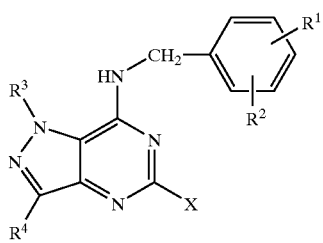

in which
R$^1$ and R$^2$ are each, independently of one another, H, A, OH, OA or Hal,
R$^1$ and R$^2$ together are alternatively alkylene having 3–5 carbon atoms, —O—CH$_2$—CH$_2$—, —CH$_2$—O—CH$_2$—, —O—CH$_2$—O— or —O—CH$_2$—CH$_2$—O—,
R$^3$ and R$^4$ are each, independently of one another, H or A,
X is R$^5$, R$^6$ or R$^7$, each of which is monosubstituted by R$^8$,
R$^5$ is linear or branched alkylene having 1–10 carbon atoms, in which one or two CH$_2$ groups may be replaced by —CH=CH— groups, O, S or SO,
R$^6$ is cycloalkyl or cycloalkylalkylene having 5–12 carbon atoms,
R$^7$ is phenyl or phenylmethyl,
R$^8$ is COOH, COOA, CONH$_2$, CONHA, CON(A)$_2$ or CN,
A is alkyl having from 1 to 6 carbon atoms, and
Hal is F, Cl, Br or I,
and physiologically acceptable salts and solvates thereof are known.

Other pyrimidine derivatives are known, for example, from EP 201 188 or WO 93/06104.

The compounds of the formula I and their salts have very valuable pharmacological properties and are well tolerated.

In particular, they exhibit specific inhibition of cGMP phosphodiesterase (PDE V).

Quinazolines having a cGMP phosphodiesterase-inhibiting activity are described, for example, in J. Med. Chem. 36, 3765 (1993) and ibid. 37, 2106 (1994).

The biological activity of the compounds of the formula I can be determined by methods as described, for example, in WO 93/06104.

The affinity of the compounds according to the invention for cGMP and cAMP phosphodiesterase is determined by measuring their IC$_{50}$ values (concentration of the inhibitor needed to achieve 50% inhibition of the enzyme activity).

The determinations can be carried out using enzymes isolated by known methods (for example W. J. Thompson et al., Biochem. 1971, 10, 311).

The experiments can be carried out using a modified batch method of W. J. Thompson and M. M. Appleman (Biochem. 1979, 18, 5228).

The compounds are therefore suitable for the treatment of illnesses of the cardiovascular system, in particular cardiac insufficiency, and for the treatment and/or therapy of potency disorders (erectile dysfunction).

The use of substituted pyrazolopyrimidinones for the treatment of impotence is described, for example, in WO 94/28902.

The compounds are effective as inhibitors of phenylephrine-induced contractions in corpus cavernosum preparations of rabbits. This biological action can be demonstrated, for example, by the method described by F. Holmquist et al. in J. Urol., 150, 1310–1315 (1993).

The inhibition of the contraction demonstrates the effectiveness of the compounds according to the invention for the therapy and/or treatment of potency disorders.

The compounds of the formula I can be employed as medicament active ingredients in human and veterinary medicine. They can furthermore be employed as intermediates in the preparation of further medicament active ingredients.

[7-(3-chloro-4-methoxybenzylamino)-1-methyl-3-propyl-1H-pyrazolo[4,3-d]-pyrimidin-5-ylmethoxy]acetic acid has proven to be a highly suitable and highly effective substance. This substance has not only a very good action in the treatment of erectile dysfunction, but can also advantageously be employed in the treatment of pulmonary hypertension.

Since this substance is very highly promising, its preparation is of extremely high interest. The preparation of this class of substances is described, for example, in EP 463756 and EP 526004.

Processes for similar intermediates are disclosed, for example, in EP 819678.

There is therefore considerable interest in finding an improved process for the preparation of [7-(3-chloro-4-methoxybenzylamino)-1-methyl-3-propyl-1H-pyrazolo[4,3-d]pyrimidin-5-ylmethoxy]acetic acid.

The object of the present invention was therefore to find a novel and effective synthesis variant for the said PDE V inhibitor.

The invention therefore relates to a process for the preparation of [7-(3-chloro-4-methoxybenzylamino)-1-methyl-3-propyl-1H-pyrazolo[4,3-d]pyrimidin-5-ylmethoxy]acetic acid

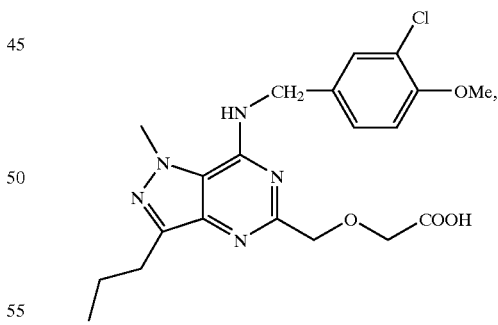

where
a) 1-methyl-3-propyl-4-amino-5-aminocarbonyl-1H-pyrazole ("Z6") is reacted with diglycolic anhydride to give [(5-aminocarbonyl-1-methyl-3-propyl-1H-pyrazol-4-ylcarbamoyl)methoxy]acetic acid ("Z7") or
a') "Z6" is reacted with a compound of the formula ("Z7B")

L—CO—CH$_2$—O—CH$_2$—COOA        "Z7B"

where L is Cl, Br, OH, SCH$_3$ or a reactive esterified OH group, and

A is alkyl having 1, 2, 3, 4, 5 or 6 carbon atoms or benzyl, to give [(5-aminocarbonyl-1-methyl-3-propyl-1H-pyrazol-4-ylcarbamoyl)-methoxy]acetic acid A ester ("Z7B"),
where A is alkyl having 1, 2, 3, 4, 5 or 6 carbon atoms or benzyl, subsequently b) "Z7" or "Z7B" is converted into (7-oxo-1-methyl-3-propyl-1H-pyrazolo[4,3-d]pyrimidin-5-ylmethoxy)acetic acid ("Z8") by cyclisation,
then c) "Z8" is converted into (7-oxo-1-methyl-3-propyl-1H-pyrazolo[4,3-d]-pyrimidin-5-ylmethoxy)acetic acid A ester ("Z9"),
where A is alkyl having 1, 2, 3, 4, 5 or 6 carbon atoms or benzyl, subsequently d) "Z9" is converted into (7-chloro-1-methyl-3-propyl-1H-pyrazolo-[4,3-d]pyrimidin-5-ylmethoxy)acetic acid A ester ("Z10"),
where A is alkyl having 1, 2, 3, 4, 5 or 6 carbon atoms
or benzyl,
by oxygen-chlorine exchange,
subsequently e) "Z10" is reacted with 3-chloro-4-methoxybenzylamine to give [7-(3-chloro-4-methoxybenzylamino)-1-methyl-3-propyl-1H-pyrazolo[4,3-d]-pyrimidin-5-ylmethoxy] acetic acid A ester ("Z 11"),
where A is alkyl having 1, 2, 3, 4, 5 or 6 carbon atoms or benzyl, and finally f) "Z11" is hydrolysed to give [7-(3-chloro-4-methoxybenzylamino)-1-methyl-3-propyl-1H-pyrazolo [4,3-d]pyrimidin-5-ylmethoxy]acetic acid ("Z12").

The starting materials for the preparation of [7-(3-chloro-4-methoxybenzylamino)-1-methyl-3-propyl-1H-pyrazolo [4,3-d]pyrimidin-5-ylmethoxy]acetic acid are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

The aminoamide "Z6" is known from the literature.

The reaction of "Z6" with diglycolic anhydride to give "Z7" is carried out in the presence or absence of an inert solvent at temperatures between about −20 and about 150°, preferably between 20 and 100°. The yields are about 90%.

The reaction of "Z6" with a compound of the formula "Z7B" is likewise carried out in the presence or absence of an inert solvent at temperatures between about −20 and about 150°, preferably between 20 and 100°. If L is a reactive esterified OH group, this is preferably alkylsulfonyloxy having 1–6 carbon atoms (preferably methylsulfonyloxy) or arylsulfonyloxy having 6–10 carbon atoms (preferably phenyl- or p-tolylsulfonyloxy, furthermore also 2-naphthalenesulfonyloxy).

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide, N-methylpyrrolidone or dimethylformamide (DMF); nitriles, such as acetonitrile; sulfoxides, such as dimethyl sulfoxide (DMSO); nitro compounds, such as nitromethane or nitrobenzene; esters, such as ethyl acetate, or mixtures of the said solvents.

The conversion of "Z7" into "Z8" is carried out in an aqueous solution of an alkali metal hydroxide or alkaline earth metal hydroxide at temperatures between about −20 and about 150°, preferably between 20 and 120°, very particularly preferably between 80° and 110°. The cyclisation is preferably carried out in aqueous NaOH or KOH solution. The yields are about 93%.

The esterification of "Z8" to "Z9" is carried out by known methods at temperatures between about −20 and about 150°, preferably between 20 and 100°, using the corresponding alcohols. The yields are about 95%.

The conversion of "Z9" into "Z10" is preferably carried out using phosphorus oxychloride (analogously to Houben Weyl E9b/2) with addition of an organic base, such as N-ethyldiisopropylamine, triethylamine, dimethylamine, pyridine or quinoline, at temperatures between about −20° and about 100°, preferably between 0° and 60°.

It is also possible to add an inert solvent, as indicated above. The yields are about 90%.

The reaction of "Z10" with 3-chloro-4-methoxybenzylamine to give "Z11" is carried out in the presence or absence of an inert solvent at temperatures between about −20 and about 150°, preferably between 20 and 100°.

The addition of an acid-binding agent, for example an alkali or alkaline earth metal hydroxide, carbonate or bicarbonate, or of another salt of a weak acid of the alkali or alkaline earth metals, preferably of potassium, sodium or calcium, or the addition of an organic base, such as triethylamine, dimethylamine, pyridine or quinoline, or of an excess of the amine component may be favourable. Suitable inert solvents are those mentioned above.

The hydrolysis of "Z11" to "Z12" can be carried out, for example, using NaOH or KOH in water, water/THF or water/dioxane at temperatures between 0 and 100°.

"Z12" can be converted into the associated acid-addition salt using a base, for example by reaction of equivalent amounts of the acid and the base in an inert solvent, such as ethanol, followed by evaporation. Suitable bases for this reaction are, in particular, those which give physiologically acceptable salts.

Thus, the acid of the formula I can be converted using a base (for example sodium hydroxide, potassium hydroxide, sodium carbonate or potassium carbonate) into the corresponding metal salt, in particular alkali metal salt or alkaline earth metal salt, or into the corresponding ammonium salt. Organic bases which give physiologically acceptable salts, such as, for example, ethanolamine, are also particularly suitable for this reaction.

The invention relates, in particular, to a process for the preparation of [7-(3-chloro-4-methoxybenzylamino)-1- methyl-3-propyl-1H-pyrazolo[4,3-d]-pyrimidin-5-ylmethoxy]acetic acid

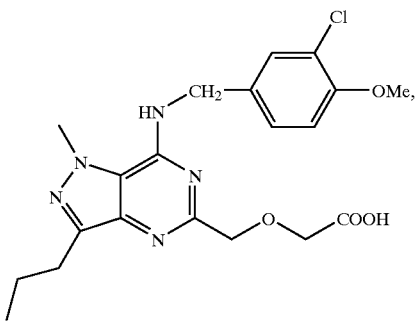

where
a) diethyl oxalate is reacted with methyl propyl ketone to give ethyl 2,4-dioxoheptanoate ("Z1"),
subsequently
b) "Z1" is converted into 3-propyl-5-ethoxycarbonyl-1H-pyrazole ("Z2"),
then
c) "Z2" is converted into 1-methyl-3-propyl-5-carboxy-1H-pyrazole ("Z3") by methylation and hydrolysis,
subsequently
d) 1-methyl-3-propyl-4-nitro-5-carboxy-1H-pyrazole ("Z4") is obtained from "Z3" by nitration,
then
e) "Z4" is converted into the carboxamide 1-methyl-3-propyl-4-nitro-5-aminocarbonyl-1H-pyrazole ("Z5"),
subsequently
f) "Z5" is converted into 1-methyl-3-propyl-4-amino-5-aminocarbonyl-1H-pyrazole ("Z6") by reduction,
then
g) 1-methyl-3-propyl-4-amino-5-aminocarbonyl-1H-pyrazole ("Z6") is reacted with diglycolic anhydride to give [(5-aminocarbonyl-1-methyl-3-propyl-1H-pyrazol-4-ylcarbamoyl)methoxy]acetic acid ("Z7") or
g') "Z6" is reacted with a compound of the formula ("Z7B")

where L is Cl, Br, OH, SCH₃ or a reactive esterified OH group, and
A is alkyl having 1, 2, 3, 4, 5 or 6 carbon atoms or benzyl, to give [(5-aminocarbonyl-1-methyl-3-propyl-1H-pyrazol-4-ylcarbamoyl)-methoxy]acetic acid A ester ("Z7B"),
where
A is alkyl having 1, 2, 3, 4, 5 or 6 carbon atoms or benzyl,
subsequently
h) "Z7" is converted into (7-oxo-1-methyl-3-propyl-1H-pyrazolo[4,3-d]-pyrimidin-5-ylmethoxy)acetic acid ("Z8") by cyclisation,
then
i) "Z8" is converted into (7-oxo-1-methyl-3-propyl-1H-pyrazolo[4,3-d]-pyrimidin-5-ylmethoxy)acetic acid A ester ("Z9"),
where
A is alkyl having 1, 2, 3, 4, 5 or 6 carbon atoms or benzyl,
subsequently
j) "Z9" is converted into (7-chloro-1-methyl-3-propyl-1H-pyrazolo-[4,3-d]pyrimidin-5-ylmethoxy)acetic acid A ester ("Z10"),
where
A is alkyl having 1, 2, 3, 4, 5 or 6 carbon atoms or benzyl, by oxygen-chlorine exchange, subsequently
k) "Z10" is reacted with 3-chloro-4-methoxybenzylamine to give [7-(3-chloro-4-methoxybenzylamino)-1-methyl-3-propyl-1H-pyrazolo[4,3-d]-pyrimidin-5-ylmethoxy] acetic acid A ester ("Z11"),
where
A is alkyl having 1, 2, 3, 4, 5 or 6 carbon atoms or benzyl, and finally
l) "Z11" is hydrolysed to give [7-(3-chloro-4-methoxybenzylamino)-1-methyl-3-propyl-1H-pyrazolo[4,3-d]pyrimidin-5-ylmethoxy]acetic acid ("Z12").
Compounds "Z1" to "Z6" are known from the literature.
The invention furthermore relates to the novel intermediates
a) [(5-aminocarbonyl-1-methyl-3-propyl-1H-pyrazol4-ylcarbamoyl)-methoxy]acetic acid;
b) [(5-aminocarbonyl-1-methyl-3-propyl-1H-pyrazol4-ylcarbamoyl)methoxy]acetic acid A ester,
where
A is alkyl having 1, 2, 3, 4, 5 or 6 carbon atoms or benzyl;
c) (7-oxo-1-methyl-3-propyl-1H-pyrazolo[4,3-d]pyrimidin-5-ylmethoxy)acetic acid;
d) (7-oxo-1-methyl-3-propyl-1H-pyrazolo[4,3-d]pyrimidin-5-ylmethoxy)acetic acid A ester,
where
A is alkyl having 1, 2, 3, 4, 5 or 6 carbon atoms or benzyl;
e) (7-chloro-1-methyl-3-propyl-1H-pyrazolo[4,3-d]pyrimidin-5-yl-methoxy)acetic acid A ester,
where
A is alkyl having 1, 2, 3, 4, 5 or 6 carbon atoms or benzyl;
f) [7-(3-chloro-4-methoxybenzylamino)-1-methyl-3-propyl-1H-pyrazolo[4,3-d]pyrimidin-5-ylmethoxy]acetic acid A ester,
where
A is alkyl having 1, 2, 3, 4, 5 or 6 carbon atoms or benzyl;
g) [7-(3-chloro-4-methoxybenzylamino)-1-methyl-3-propyl-1H-pyrazolo[4,3-d]pyrimidin-5-ylmethoxy]acetic acid,
and salts and solvates thereof.

The starting materials for the preparation of [7-(3-chloro-4-methoxy-benzylamino)-1-methyl-3-propyl-1H-pyrazolo[4,3-d]pyrimidin-5-yl-methoxy]acetic acid are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

The term "solvates of the compounds of the formula I" is taken to mean adductions of inert solvent molecules onto the compounds of the formula I which form owing to their mutual attractive force. Solvates are, for example, mono- or dihydrates or alcoholates.

A is alkyl having 1–6 carbon atoms.

In the above compounds, alkyl is preferably unbranched and has 1, 2, 3, 4, 5 or 6 carbon atoms and is preferably methyl, ethyl or propyl, furthermore preferably isopropyl, butyl, isobutyl, sec-butyl or tert-butyl, but also n-pentyl, neopentyl, isopentyl or hexyl.

Above and below, all temperatures are given in ° C. In the following examples, "conventional work-up" means that water is added if necessary, the pH is adjusted, if necessary, to between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation.

Mass spectrometry (MS):
EI (electron impact ionisation) M+
FAB (fast atom bombardment) (M+H)+

EXAMPLE 1

1.1 13.5 g of diglycolic anhydride are added at 15° to a solution of 20.5 g of 1-methyl-3-propyl4-amino-5-aminocarbonyl-1H-pyrazole ("Z6") in 400 ml of dichloromethane, and the mixture is stirred for a further 1 hour. The mixture is subjected to conventional work-up, giving 32.5 g of [(5-aminocarbonyl-1-methyl-3-propyl-1H-pyrazol4-ylcarbamoyl)methoxy]-acetic acid ("Z7").

1.2 A solution of 10.0 g of "Z7" and 3.9 g of NaOH in 217 ml of water is heated at 95° for 1.5 hours. The mixture is cooled and subjected to conventional work-up, giving 9 g of (7-oxo-1-methyl-3-propyl-1H-pyrazolo-[4,3-d]pyrimidin-5-ylmethoxy)acetic acid ("Z8").

1.3 0.3 ml of sulfuric acid (95–97%) is added to a solution of 7.0 g of "Z8" in 80 ml of ethanol, and the mixture is refluxed for 2 hours. The solvent is removed, and the mixture is subjected to conventional work-up, giving 7 g of ethyl (7-oxo-1-methyl-3-propyl-1H-pyrazolo[4,3-d]pyrimidin-5-ylmethoxy)acetate.

1.4 110 ml of phosphoryl chloride are added to 14.8 g of ethyl (7-oxo-1-methyl-3-propyl-1H-pyrazolo[4,3-d]pyrimidin-5-ylmethoxy)acetate, then 9.5 ml of N-ethyidiisopropylamine are added at 10° with stirring, and the mixture is stirred at 50° for a further 3 hours.

The solvents are removed, then ice-water is added, and the mixture is subjected to conventional work-up, giving 14 g of ethyl (7-chloro-1-methyl-3-propyl-1H-pyrazolo[4,3-d]pyrimidin-5-ylmethoxy)acetate as an oil.

1.5a 3 g of ethyl (7-chloro-1-methyl-3-propyl-1H-pyrazolo-[4,3-d]pyrimidin-5-ylmethoxy)acetate and 1.9 g of 3-chloro-4-methoxy-benzylamine in 50 ml of dimethylformamide (DMF) are stirred at 60° for 12 hours in the presence of potassium carbonate. After filtration, the solvent is removed, and the mixture is subjected to conventional work-up, giving 4.6 g of ethyl [7-(3-chloro-4-methoxybenzylamino)-1-methyl-3-propyl-1H-pyrazolo[4,3-d]pyrimidin-5-ylmethoxy]acetate.

or 1.5b

A mixture of 1.8 g of ethyl (7-chloro-1-methyl-3-propyl-1H-pyrazolo-[4,3-d]pyrimidin-5-ylmethoxy)acetate and 1.5 g of 3-chloro-4-methoxy-benzylamine in 20 ml of N-methylpyrrolidone is warmed at 110° for 4 hours. After cooling, the mixture is subjected to conventional work-up, giving 2.2 g of ethyl [7-(3-chloro-4-methoxybenzylamino-1-methyl-3-propyl-1H-pyrazolo[4,3-d]pyrimidin-5-ylmethoxy]acetate.

1.6 4.3 g of ethyl [7-(3-chloro-4-methoxybenzylamino)-1-methyl-3-propyl-1H-pyrazolo[4,3-d]pyrimidin-5-ylmethoxy]acetate are dissolved in 30 ml of tetrahydrofuran (THF), 10 ml of 10% NaOH are added, and the mixture is stirred at 60° for 8 hours. After 10% HCl has been added, the deposited crystals are separated off and recrystallised from methanol, giving 3.7 g of [7-(3-chloro-4-methoxybenzylamino)-1-methyl-3-propyl-1H-pyrazolo[4,3-d]pyrimidin-5-ylmethoxy]acetic acid.

Evaporation with the equivalent amount of ethanolamine in methanol gives [7-(3-chloro-4-methoxybenzylamino)-1-methyl-3-propyl-1H-pyrazolo[4,3-d]-pyrimidin-5-ylmethoxy]acetic acid, ethanolamine salt, m.p. 138°.

What is claimed is:

1. A Compound which is
   a) [(5-aminocarbonyl-1-methyl-3-propyl-1H-pyrazol-4-ylcarbamoyl)methoxy]acetic acid;
   b) [(5-aminocarbonyl-1-methyl-3-propyl-1H-pyrazol-4-ylcarbamoyl)methoxy]acetic acid A ester,
      where
      A is alkyl having 1, 2, 3, 4, 5 or 6 carbon atoms or benzyl;
   c) (7-oxo-1-methyl-3-propyl-1H-pyrazolo[4,3-d]pyrimidin-5-ylmethoxy)actic acid;
   d) (7-oxo-1-methyl-3-propyl-1H-pyrazolo[4,3-d]pyrimidin-5-ylmethoxy)acetic acid A ester,
      where
      A is alkyl having 1, 2, 3, 4, 5 or 6 carbon atoms or benzyl;
   e) (7-chloro-1-methyl-3-propyl-1H-pyrazolo[4,3-d]pyrimidin-5-ylmethoxy)acetic acid A ester,
      where
      A is alkyl having 1, 2, 3, 4, 5 or 6 carbon atoms or benzyl;
   f) [7-(3-chloro-4-methoxybenzylamino)-1-methyl-3-propyl-1H-pyrazolo[4,3-d]pyrimidin-5-ylmethoxy] acetic acid A ester,
      where
      A is alkyl having 1, 2, 3, 4, 5 or 6 carbon atoms or benzyl;
   g) [7-(3-chloro-4-methoxybenzylamino)-1-methyl-3-propyl-1H-pyrazolo[4,3-d]pyrimidin-5-ylmethoxy] acetic acid, or a salt thereof.

2. A compound according to claim 1, which is
   a) ethyl [(5-aminocarbonyl-1-methyl-3-propyl-1H-pyrazol-4-ylcarbamoyl)methoxy]acetate;
   b) ethyl (7-oxo-1-methyl-3-propyl-1H-pyrazolo[4,3-d]pyrimidin-5-ylmethoxy)acetate;
   c) ethyl (7-chloro-1-methyl-3-propyl-1H-pyrazolo[4,3-d]pyrimidin-5-ylmethoxy)acetate;
   d) ethyl [7-(3-chloro-4-methoxybenzylamino)-1-methyl-3-propyl-1H-pyrazolo[4,3-d]pyrimidin-5-ylmethoxy] acetate;
   or a salt thereof.

3. A process for the preparation of [7-(3-chloro-4-methoxybenzylamino)-1-methyl-3propyl-1H-pyrazolo[4,3d]pyrimidin-5-ylmethoxy]acetic acid

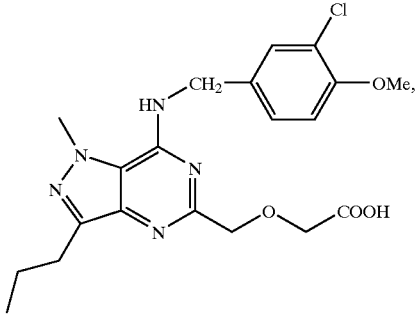

comprising
   a) reacting 1-methyl-3- propyl-4-amino-5-aminocarbonyl-1H-pyrazole ("Z6") with diglycolic anhydride to give [(5-aminocarbonyl-1-methy-3- propyl-1H-pyrazol-4-ylcarbamoyl)methoxy]acetic acid ("Z7") or a') reacting "Z6" with a compound of the formula ("Z7B")

L—CO—CH$_2$—O—CH$_2$—COOA        "Z7B"

where L is Cl, Br, OH, SCH$_3$ or a reactive esterified OH group, and

A is alkyl having 1, 2, 3, 4, 5 or 6 carbon atoms or benzyl, to give [(5-aminocarbonyl-1-methyl-3-propyl-1H-pyrazol-4-ylcarbamoyl)methoxy]acetic acid A ester ("Z7B"), where A is alkyl having 1, 2, 3, 4, 5 or 6 carbon atoms or benzyl, subsequently b) converting "Z7" or "Z7B" into (7-oxo-1-methyl-3-propyl-1H-pyrazolo [4,3-d]pyrimidin-5-ylmethoxy)acetic acid ("Z8") by cyclization, then c) converting "Z8" into (7-oxo-1-methyl-3-propyl-1H-pyrazolo[4,3d]-pyrimidin-5-ylmethoxy)acetic acid A ester ("Z9"), where A is alkyl having 1, 2, 3, 4, 5 or 6 carbon atoms or benzyl, subsequently d) converting "Z9" into (7-chloro-1-methyl-3-propyl-1H-pyrazo[4,3-d]pyrimidin-5-ylmethoxy)acetic acid A ester ("Z10"), where A is alkyl having 1, 2, 3, 4, 5 or 6 carbon atoms or benzyl, by oxygen-chlorine exchange, subsequently e) reacting "Z10" with 3-chloro-4-methoxybenzylamine to give [7-(3-chloro-4-methoxybenzylamin)-1-methyl-3-propyl-1H-pyrazolo[4,3-d]pyrimidin-5-ylmethoxy] acetic acid A ester ("Z11"), where A is alkyl having 1, 2, 3, 4, 5 or 6 carbon atoms or benzyl, and finally f) hydrolyzing "Z11" to give [7-(3-chloro-4-methoxybenzylamino)-1-methyl-3-propyl-1H-pyrazolo[4,3-d]pyrimidin-5-ylmethoxy]acetic acid ("Z12").

4. A process for the preparation of [7-(3-chloro-4-methoxybenzylamino)-1-methyl-3-propyl-1H-pyrazolo[4,3-d]pyrimidin-5-ylmethoxy]acetic acid

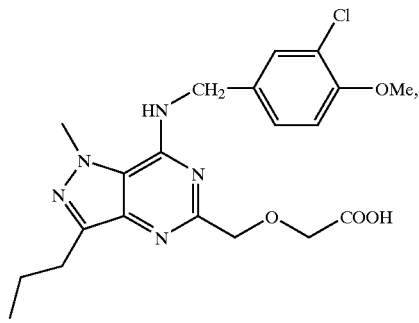

comprising a) reacting diethyl oxalate with methyl propyl ketone to give ethyl 2,4-dioxoheptanoate ("Z1"), subsequently b) converting "Z1" into 3-propyl-5-ethoxycarbonyl-1H-pyrazole ("Z2"), then c) converting "Z2" into 1-methyl-3-propyl-5-carboxy-1H-pyrazole ("Z3") by methylation and hydrolysis, subsequently d) nitrating "Z3" to obtain 1-methyl-3-propyl-4-nitro-5-caraboxy-1H-pyrazole ("Z4"), then e) converting "Z4" into the carboxamide 1-methy-3-3-propy-4-nitro-5-aminocarbonyl-1H-pyrazole ("Z5"), subsequently f) converting "Z5" into 1-methyl-3-propyl-4-amino-5-aminocarbonyly-1H-pyrazole ("Z6") by reduction, then g) reacting 1-methyl-3-propyl-4-amino-5-aminocarbonyl-1H-pyrazole ("Z6") with diglycolic anhydride to give [(5-aminocarbonyl-1-methyl-3-propyl-1H-pyrazol-4-ylcarbamoyl)metboxy]acetic acid ("Z7") or g') reacting "Z6" with a compound of the formula ("Z7B")

L—CO—CH$_2$—O—CH$_2$—COOA        "Z7B"

where L is Cl, Br, OH, SCH$_3$ or a reactive esterified OH group, and

A is alkyl having 1, 2, 3, 4, 5 or 6 carbon atoms or benzyl, to give [(5-aminocarbonyl-1-methyl-3-propyl-1H-pyrazol-4-ylcarbamoyl)methoxy]acetic acid A ester ("Z7B"), where A is alkyl having 1, 2, 3, 4, 5 or 6 carbon atoms or benzyl, subsequently h) converting "Z7" into (7-oxo-1-methyl-3-propyl-1H-pyrazolo[4,3-d]pyrimidin-5-ylmethoxy)acetic acid ("Z8") by cyclisation, then i) converting "Z8" into (7-oxo-1-methyl-3-propyl-1H-pyrazolo[4,3-d]pyrimidin-5-ylmethoxy)acetic acid A ester ("Z9"), where A is alkyl having 1, 2, 3,4, 5 or 6 carbon atoms or benzyl, subsequently
- j) converting "Z9" into (7-chloro-1-methyl-3-propyl-1H-pyrazolo[4,3-d]pyrimidin-5-ylmethoxy)acetic acid A ester ("Z10"),
  where
  A is alkyl having 1, 2, 3, 4, 5 or 6 carbon atoms or benzyl,
by oxygen-chlorine exchange,
subsequently
- k) reactin "Z10" with 3-chloro-4-methoxybenzylamine to give [7-(3-chloro-4-methoxybenzylamino)-1-methyl-3-propyl-1H-pyrazolo[4,3-d]pyrimidin-5-ylmethoxy]acetic acid A ester ("Z11"),
  where
  A is alkyl having 1, 2, 3, 4, 5 or 6 carbon atoms or benzyl,
and finally
- l) hydrolyzing "Z11" to give [7-(3-chloro-4-methoxybenzylamino)-1-methyl-3-propyl-1H-pyrazolo[4,3-d]pyrimidin-5-ylmethoxy]acetic acid ("Z12").

* * * * *

UNITED STATES PATENT AND TRADEMARK OFFICE
CERTIFICATE OF CORRECTION

PATENT NO.        : 6,960,661 B2                              Page 1 of 1
APPLICATION NO. : 10/470337
DATED             : November 1, 2005
INVENTOR(S)      : Hans-Michael Eggenweiler It is certified that error appears in the above-identified patent and that said Letters Patent is hereby corrected as shown below:

Title page, Foreign Application Priority Data, reads "Mar. 27, 2001" should read -- Jan. 27, 2001 --
Column 8, line 14, reads "actic acid" should read -- acetic acid --
Column 8, line 47, reads "-3propyl-" should read -- -3-propyl- --
Column 8, line 48, reads "3d]pyrimidin-" should read -- 3-d]pyrimidin- --
Column 8, line 67, reads "1-methy-3-" should read -- 1-methyl-3- --
Column 9, line 30, reads "pyrazolo[4,3d]-pyrimidin" should read -- pyrazolo[4,3-d] pyrimidin --
Column 9, line 40, reads "pyrazo[4,3-d]" should read -- pyrazolo[4,3-d]
Column 9, line 51, reads "methoxybenzylamin" should read -- methoxybenzylamino --
Column 10, line 27, reads "caraboxy" should read -- carboxy --
Column 10, line 30 and 31, read "1-methy-3-3-propy" should read
-- 1-methyl-3-3-propyl --
Column 10, line 34, reads "aminocarbonyly" should read -- aminocarbonyl --
Column 10, line 39, reads "metboxy" should read -- methoxy --
Column 10, line 66, reads "3,4" should read -- 3, 4 --
Column 11, line 10, reads "reactin" should read -- reacting --

Signed and Sealed this

Twenty-fifth Day of July, 2006

JON W. DUDAS
*Director of the United States Patent and Trademark Office*